United States Patent
Ibrahim et al.

(10) Patent No.: US 7,112,323 B2
(45) Date of Patent: Sep. 26, 2006

(54) INTRACELLULAR PROTEINACIOUS ANTIMICROBIAL AGENTS FROM LACTIC ACID BACTERIA DERIVED FROM FERMENTED FOOD SAMPLES

(75) Inventors: Osama O. Ibrahim, Gurnee, IL (US); Ahmed E. Yousef, Columbus, OH (US); Hyun-Jung Chung, Columbus, OH (US)

(73) Assignee: Kraft Foods Holdings, Inc., Northfield, IL (US)

( * ) Notice: Subject to any disclaimer, the term of this patent is extended or adjusted under 35 U.S.C. 154(b) by 254 days.

(21) Appl. No.: 10/430,381

(22) Filed: May 7, 2003

(65) Prior Publication Data
US 2004/0223955 A1   Nov. 11, 2004

(51) Int. Cl.
*A01N 63/00* (2006.01)
(52) U.S. Cl. .................. 424/93.45; 426/61; 426/321; 426/324; 426/326
(58) Field of Classification Search ................. 426/61, 426/321, 324, 326; 424/93.45
See application file for complete search history.

(56) References Cited

U.S. PATENT DOCUMENTS

| 2,744,827 A | 5/1956 | Mattick et al. |
| 4,584,199 A | 4/1986 | Taylor |
| 4,597,972 A | 7/1986 | Taylor |
| 5,096,718 A | 3/1992 | Ayres et al. |
| 5,260,061 A | 11/1993 | Ayres et al. |
| 5,348,881 A | 9/1994 | Vedamuthu et al. |
| 5,527,505 A | 6/1996 | Yamauchi et al. |
| 5,573,797 A | 11/1996 | Wilhoit |
| 5,573,801 A | 11/1996 | Wilhoit |
| 5,593,800 A | 1/1997 | Fujioka et al. |
| 6,150,139 A | 11/2000 | Mollet et al. |
| 6,207,411 B1 | 3/2001 | Ross et al. |

FOREIGN PATENT DOCUMENTS

| EP | 0 333 056 | 9/1989 |
| JP | 40230010 | * 12/1990 |
| JP | 405084092 | * 6/1993 |
| JP | 94034709 | * 5/1994 |

OTHER PUBLICATIONS

Kim et al., "A Study on Growth Inhibition of *Escherichia coli* and *Salmonella Typhimurium* by Lactid Acid Bacteria", *J. Animal Science and Technology (Korea)*, vol. 44, No. 4, 491-498 (Aug. 2002).

Lee et al., "Physiological Characteristics of Lactic Acid Bacteria Isolated from *Kimchi* to Select Starter of Fermented Sausage", *J. Animal Science and Technology (Korean)*, vol. 43, No. 3, 393-400 (Jun. 2001).

Miteva, V., "Detection and Characterization of a Novel Antibacterial Substance Produced by a *Lactobacillus Delbrueckii* Strain 1043", *Journal of Applied Microbiology*, vol. 85, 603-614 (Sep. 1998).

Caridi, A., "Identification and First Characterization of Lactic Acid Bacteria Isolated from the Artisanal Ovine Cheese Percorino del Poro", *International Journal of Dairy Technology*, vol. 56, No. 2, 105-110 (May 2003).

Kim, S-K. et al, "Bacteriocin Produced by *Lactobacillus Curvatus* SE1 Isolated from Kimchi", *Journal of Microbiology and Biotechnology*, vol. 8, No. 6, 588-594 (Dec. 1998).

Choi et al., Journal of Applied Microbiology, Production of a nisin-like bacteriocin by *Lactococcus lactis* subsp. lactis A164 isolated from Kimchi, 88:563-571 (2000).

Giometti et al., Antimicrobial Agents & Chemotherapy, In Vitro Activities of Membrane-Active Peptides against Gram-Positive and Gram-Negative Aerobic Bacteria, 42:3320-3324 (1998).

Bechard et al. Journal of Agricultural Food Chemistry, Isolation and Partial Chemical Characterization of an Antimicrobial Peptide Produced by a Strain of *Bacillus subtilis*, 46:5355-5361 (1998).

Hwang et al. Molecular Biotechnology, A Simple Method for the Purification of an Antimicrobial Peptide in Recombinant *Escherichia coli*, 18:194-198 (2001).

* cited by examiner

Primary Examiner—Herbert J. Lilling
(74) Attorney, Agent, or Firm—Fitch, Even, Tabin & Flannery

(57) ABSTRACT

The present invention is directed bacterial isolates that produce proteinacious antimicrobial agents effective against a variety of food borne pathogens. The invention includes the bacteria, bacteriocin preparations derived from the bacteria and methods by which the preparations may be used.

7 Claims, No Drawings

INTRACELLULAR PROTEINACIOUS ANTIMICROBIAL AGENTS FROM LACTIC ACID BACTERIA DERIVED FROM FERMENTED FOOD SAMPLES

FIELD OF THE INVENTION

The present invention relates to specific lactic acid bacteria that produce protease-sensitive antimicrobial agents. The bacteria and compositions derived from the bacteria may be used as additives in foods and pharmaceuticals to prevent the growth of a wide variety of bacterial pathogens.

BACKGROUND OF THE INVENTION

Bacterial contamination of foods is known to be responsible for spoilage and for the transmission of food borne illness. This problem is particularly acute in ready to eat meats and dairy products which are not normally reheated by consumers prior to ingestion. As a result, a great deal of effort has been expended in attempts to identify low cost natural products that can be safely added to foods for the purpose of inhibiting bacterial growth.

Bacteriocins are antimicrobial peptides that are produced by bacteria and which have a bactericidal or bacteristatic action against closely related species. The most extensively characterized bacteriocin is nisin which is produced by a lactic acid type bacteria and which may be used to prevent the growth of Gram-positive bacteria in a variety of different food products (see e.g., U.S. Pat. No. 2,744,827; U.S. Pat. No. 4,584,199; U.S. Pat. No. 4,597,972 and U.S. Pat. No. 5,527,505). Bacterial species used for the isolation of bacteriocins have included propionic acid bacteria (U.S. Pat. Nos. 5,096,718; 5,260,061), *Streptococcus* or *Pediococcus* bacteria (U.S. Pat. Nos. 5,573,797; 5,593,800; 5,573,801), and *Micrococcus varians* (U.S. Pat. No. 6,150,139).

Although several bacteriocins have been identified, those that are effective against Gram-negative bacteria are relatively rare. Thus, the identification of new bacteriocin compounds of this type is of importance in extending our ability to protect foods and other compositions. Ideally, these peptides should be safe, have a broad spectrum of activity and be stable over a wide range of pHs and temperatures.

SUMMARY OF THE INVENTION

The present invention is based upon the discovery of bacterial isolates that produce bacteriocins inhibiting the growth of both Gram-negative and Gram-positive bacteria. The bacteria, and the extracts derived from the bacteria, may be used as antimicrobial agents in both dietary and pharmaceutical compositions.

In its first aspect, the invention is directed to biologically pure *Lactobacillus curvatus* bacteria having all of the identifying characteristics of the bacteria that has been deposited as PTA-5150. The term "biologically pure" refers to preparations in which PTA-5150 bacteria are essentially the only type present. Other types of bacteria in the preparations should constitute 10%, and preferably less, of the total population. The identifying characteristics of PTA-5150 bacteria are that they are of the species *Lactobacillus curvatus* and produce a bacteriocin acting to preferentially inhibit the growth of Gram-negative organisms. The bacteriocin has been found to be effective against the growth of *Salmonella typhimurium*, *Salmonella entertides*, and *Escherichia coli* O157:H7.

In addition, the invention is directed to biologically pure *Lactobacillus casei* bacteria having all of the identifying characteristics of the bacteria deposited as PTA-5149. In this case, identifying characteristics include the ability to produce a bacteriocide that is effective against both Gram-negative and Gram-positive bacteria and a microbial taxonomy indicating that the bacteria are *Lactobacillus casei*.

In another aspect, the invention is directed to methods of producing a bacteriocin composition by culturing the cells described above and then preparing a cell-free extract of the cultures. The invention includes the cell-free extract itself and methods of reducing the growth of various types of microbes in dietary and pharmaceutical compositions by adding either the bacteria or the bacterial extract. These methods should be particularly effective in compositions subject to contamination with Gram-negative bacteria and, unlike procedures involving other bacteriocin compositions, should remain effective in the absence of added chelating agents. The present bacteriocins are effective when used in compositions that are heated (e.g. at 70–100 degrees Celsius for 10 minutes–5 hours or more), or that have a basic pH (i.e., from 7.0–12.0). They should also be effective when used in dairy products or ready to eat meats.

DETAILED DESCRIPTION OF THE INVENTION

The present invention is directed to two specific bacterial isolates that have been found to produce proteinacious antimicrobial agents effective against a variety of food borne pathogens. One of the isolates was derived from Kimchi and was characterized as *Lactobacillus curvatus*. Although extracts from this isolate were initially thought to be only effective against Gram-negative bacteria, subsequent experiments indicated that they also have some effect against Gram-positive bacteria. The other isolate was derived from Danish blue cheese and was characterized as *Lactobacillus casei*. These bacteria were deposited on Apr. 23, 2003 according to the terms of the Budapest Treaty. Deposit took place at the American Type Culture Collection, 10801 University Blvd., Manassas, Va. 20110-2209, USA. The deposits were given the numbers PTA-5150 and PTA-5149 respectively.

One of the main defining characteristics of the present bacterial isolates is that they produce an antimicrobial agent that is effective against Gram-negative bacteria. Screening for isolates producing such an effect may be accomplished using essentially the procedure described by Choi et al. (*J. App. Microbiol.* 88:563–571 (2000)). This involves extracting a food source using a liquid medium that maintains bacterial integrity. The extract may be made cell-free using methods that are well known in the art and then tested for antimicrobial activity. One way to perform such a test is to add samples of extract to wells created in an agar bacterial growth plate which includes a Gram-negative indicator strain such as *E. coli* P220. The presence of antimicrobial activity is evidenced by a zone surrounding individual wells where the growth of the indicator bacteria has been inhibited.

The active agents in the cell-free extracts were found to be sensitive to treatment by protease, suggesting that they are bacteriocins. These agents have a number of characteristics that suggest that they will be valuable as antimicrobial additives for a variety of compositions, including food and pharmaceutical products. For example, the bacteriocins derived from both *L. curvatus* and *L. casei* remain effective at high temperatures. Thus, they should be useful in retarding the growth of pathogens in compositions undergoing heating such as food products that must be cooked or pharmaceutical compositions that must undergo heating as part of the process by which they are prepared.

Bacteriocin preparations of the present invention are also active in a very wide range of pH values (at least from pH 2 to pH 12). This suggests that the active agents are extremely stable and can be used in food and pharmaceutical compositions of nearly any acidity. It is possible that the agents may even remain effective for a period of time in the stomach of individuals after ingestion.

In addition, cell-free extracts derived from both isolates have been found to be effective against some types of bacteria that are known to cause serious illness. Since the extracts differ in their ability to retard the growth of different type of microbes, combining preparations should broaden the spectrum of antimicrobial activity available and provide better overall protection.

The exact amount of bacteriocin composition to be added to a food or pharmaceutical can be determined using methods that are well known in the art and will depend upon a number of factors, including the type of bacterial contamination likely to occur in a preparation. The bacteriocins may be used either alone or in combination with other bacteriocins or antibiotics.

The procedures needed for storing, growing, harvesting and processing lactic acid bacteria are well known in the art and can be used for the isolates described above. Methods for characterizing, purifying and using bacteriocins are also well known (see e.g. Giacometti et al. *Antimicrobial Agents & Chemotherapy* 42:3320–3324 (1998); Bechard et al. *J. Agric. Food Chem.* 46:5355–5361 (1998); Hwang et al. *Molec. Biotech.* 18:194–198 (2001); U.S. Pat. No. 6,207,411; U.S. Pat. No. 6,150,139; and U.S. Pat. No. 5,348,881) and can be applied to the extracts of the present invention.

EXAMPLES

Example 1

Identification of Bacteria

Various fermented food products were screened in order to search for lactic acid bacteria producing proteinacious antimicrobial agents against food borne pathogens. It was found that eight isolates from Kimchi (Korean fermented vegetable) showed inhibitory activity against *E. coli* P220, a Gram-negative bacteria. A selected isolate from these eight was identified by microbial taxonomy to be *Lactobacillus curvatus*. Initial experiments suggested that a cell-free extract prepared from this isolate had antimicrobial activity against Gram-negative bacteria of *Salmonella typhimurium, Salmonella enteritidis, Escherichia coli* O157:H7, but little or no microbial activity against Gram-positive bacteria of *Listeria monocytogenes* Scott A, *Listeri innocua*, and *Lactococcus lactis*. These results indicate that the isolate produces a relatively narrow spectrum intracellular antimicrobial agent preferentially active against Gram-negative bacteria. Protease sensitivity assays showed that the antimicrobial activity was inhibited by treatment with the enzyme pronase, an indication that the antimicrobial substance is proteinacious, (i.e., a bacteriocin). The bacterial isolate was deposited on Apr. 23, 2003 under the terms of the Budapest treaty at the American Type Culture Collection, 10801 University Blvd., Manassas, Va. 20110-2209, USA. It was assigned deposit number PTA-5150.

In additional experiments, four isolates derived from Danish blue cheese were found to inhibit the growth of *E. coli* P220. A selected isolate was identified by microbial taxonomy to be *Lactobacillus casei*. Cell-free extract from the isolate showed antimicrobial activity against Gram-negative bacteria of *Salmonella lyphimurium, Salmonella enteritidis, Escherichia coli* O157:H7 and against Gram-positive bacteria of *Listeria monocytogenes* Scott A, *Listeria innocua*. These results suggest that the isolate produces a wide spectrum intracellular antimicrobial agent effective against both Gram-negative and Gram-positive bacteria. Protease sensitivity assays indicated that antimicrobial activity was inhibited by treatment with the enzyme pepsin. This again suggests that the antimicrobial substance produced by the bacteria is proteinacious (i.e., a bacteriocin.) This bacterial isolate was deposited on Apr. 23, 2003 under the terms of the Budapest treaty at the American Type Culture Collection, 10801 University Blvd., Manassas, Va. 20110-2209, USA. It was assigned deposit number PTA-5149.

Example 2

Characterization of Antimicrobial Agents in Cell-free Extracts

As discussed above, two lactic acid bacteria isolates were identified by both fatty acid profile and ribosomal RNA typing as *Lactobacillus curvatus* and *Lactobacillus casei*. These isolates were obtained from Kimchi and Danish blue cheese respectively. Both isolates were propagated overnight at 30° C. in MRS broth supplemented with 1% sodium chloride. Harvested cells were treated with lysozyme and sonicated. Analysis of the cell-free extracts (CFE) demonstrated that the two bacterial isolates produce intracellular proteinacious microbial agents that are effective against food borne pathogens.

The cell-free extracts of the *L. curvatus* and *L. casei* bacterial isolates were found to share a number of common properties. In particular, they were found to have antimicrobial activity against Gram-negative bacteria without the need of chelating agents such as EDTA. In this respect, the active agents in the cell-free extracts differ from traditional antimicrobial peptides (e.g., nisin).

Cell-free extracts from both bacterial isolates were found to maintain their antimicrobial activity at high temperatures. In the case of *L. curvatus*, activity was maintained against *E. coli* P200 even after extracts were heated to a temperature of 70° C. for ten minutes. In the case of *L. casei*, activity was maintained after heating preparations to 100° C. for ten minutes.

Cell-free extracts were also found to maintain antimicrobial activity after exposure to a wide range of pHs (pH 2 to pH 12). Stability to this range of pHs is an unusual property; commercial bacteriocins are typically only stable at acidic pH values. The results suggest that the antimicrobial agents produced by the *L. curvatus* and *L. casei* isolates will be useful in both acidic and non-acid food products.

The antimicrobial activity produced by the present isolates was found to be effective against a diverse group of food borne pathogens. These include *Escherichia coli* p220, *Escherichia coli* K12, *Escherichia coli* O157: H7, *Salmonella enteritidis, Salmonella typhimurium, Pseudomonas fluorescens, Listeria monocytogenes* Scott A and *Bacillus cereus*. Thus, it is clear that the cell-free extracts produce a broad spectrum of antimicrobial activity against both Gram-positive and Gram-negative bacteria. This activity is summarized in table 1.

TABLE 1

| Target species | Lactobacillus casei | Lactobacillus curvatus |
|---|---|---|
| Escherichia coli p220 | + + | + + |
| Eseherichia coli O157:H7 | + | + |
| Salmonella enteritidis | + + | + |
| Pseudomonas fluorescence | + | + + |
| Listeria monocytogenes Scott A | + + + | ± |
| Bacillus cereus | + + + | ± |

In other experiments, cell-free extracts from the *L. curvatus* and *L. casei* isolates had an inhibitory effect the against Gram-negative indicator bacteria, *E. Coli* p220, in three filtered food samples. These samples were wiener exudates, milk permeate and cheese whey. The data indicate that components present in the filtered food samples did not neutralize the antimicrobial activity in the cell-free extract. Thus, the active agents in the extracts should be effective with these types of food preparations. In addition, the cell-free extract from *L. casei* was found to have a synergistic effect when combined with high pressure processing technology against a Gram-positive bacterium, *Listeria monocytogenes*, in buffer solution and in a food matrix (hotdogs). This is an indication that the active agent in the cell-free extract should be effective when used in certain processing procedures for these types of food products.

All references cited herein are fully incorporated by reference. Having now fully described the invention, it will be understood by those of skill in the art that the invention may be performed within a wide and equivalent range of conditions, parameters and the like, without effecting the spirit or scope of the invention or any embodiment thereof.

What is claimed is:

1. A method of reducing the growth of a microbe in a food or pharmaceutical composition, comprising adding a biologically pure *Lactobacillus curvatus* bacteria having all of the identifying characteristics of the bacteria deposited on Apr. 23, 2004 as PTA-5150 at American Type Culture Collection, 10801 University Boulevard, Manassas, Va. 20110-2209 to said composition.

2. The method of claim 1, wherein said microbe is a Gram-negative bacterium.

3. The method of claim 2, wherein said bacteria is added without the addition of a chelating agent.

4. The method of claim 1, wherein said microbe is a bacterium selected from the group consisting of: *Escherichia coil* p220; *Escherichia coil* K12; *Escherichia coil* O157:H7; *Salmonella enteritidis*; *Salmonella typhimurium*; *Pseudomonas fluorescens*; *Listeria monocytogenes* Scott A; and *Bacillus cereus*.

5. The method of claim 1, wherein said food or pharmaceutical composition is heated to at least a temperature of 70° C. for at least 10 minutes after the addition of said bacteria.

6. The method of claim 1, wherein said food or pharmaceutical composition has a pH of greater than 7.0 and less than 12.0.

7. The method of claim 1, wherein said bacteria is added to a dairy or meat product.

* * * * *

UNITED STATES PATENT AND TRADEMARK OFFICE
CERTIFICATE OF CORRECTION

| | | |
|---|---|---|
| PATENT NO. | : 7,112,323 B2 | Page 1 of 1 |
| APPLICATION NO. | : 10/430381 | |
| DATED | : September 26, 2006 | |
| INVENTOR(S) | : Ibrahim et al. | |

It is certified that error appears in the above-identified patent and that said Letters Patent is hereby corrected as shown below:

- On Title page, col. 2 (Other Publications), line 2, delete "Lactid Acid" and insert -- Lactic Acid -- .

- In col. 6, lines 18-19, in Claim 4, delete "Escherichia coil p220" and insert -- Escherichia coli p220 -- .

- In col. 6, line 19, in Claim 4, delete "Escherichia coil K12" and insert -- Escherichia coli K12 -- .

- In col. 6, lines 19-20, in Claim 4, delete "Escherichia coil O157:H7" and insert -- Escherichia coli O157:H7 -- .

Signed and Sealed this

Third Day of April, 2007

JON W. DUDAS
*Director of the United States Patent and Trademark Office*